United States Patent [19]
Kaplan et al.

[11] Patent Number: 5,941,868
[45] Date of Patent: Aug. 24, 1999

[54] LOCALIZED INTRAVASCULAR DELIVERY OF GROWTH FACTORS FOR PROMOTION OF ANGIOGENESIS

[75] Inventors: Aaron V. Kaplan, Los Altos, Calif.; Michael Simons, Chestnut Hill, Mass.

[73] Assignees: Localmed, Inc., Palo Alto, Calif.; Beth Israel Deaconess Medical Center, Boston, Mass.

[21] Appl. No.: 08/753,224

[22] Filed: Nov. 22, 1996

Related U.S. Application Data

[60] Provisional application No. 60/009,086, Dec. 22, 1995.

[51] Int. Cl.$^6$ ................................................ A61M 31/00
[52] U.S. Cl. ............................................................ 604/500
[58] Field of Search ................................ 604/96, 101, 99, 604/265, 266, 890.1, 892.1, 52, 53; 606/192, 194

[56] References Cited

U.S. PATENT DOCUMENTS

| | | |
|---|---|---|
| 5,021,044 | 6/1991 | Sharkawy . |
| 5,049,132 | 9/1991 | Shaffet et al. . |
| 5,171,217 | 12/1992 | March et al. . |
| 5,180,366 | 1/1993 | Woods . |
| 5,244,460 | 9/1993 | Unger et al. . |
| 5,652,225 | 7/1997 | Isner . |

FOREIGN PATENT DOCUMENTS

| | | | |
|---|---|---|---|
| WO 90/11734 | 10/1990 | WIPO | ................................ A61F 2/06 |
| WO 92/11895 | 7/1992 | WIPO | ........................... A61M 31/00 |
| WO 93/08866 | 5/1993 | WIPO | ........................... A61M 29/00 |
| WO 95/05864 | 3/1995 | WIPO | ........................... A61M 25/00 |
| WO 96/26742 | 9/1996 | WIPO | ............................ A61K 48/00 |
| WO 96/39830 | 12/1996 | WIPO | ........................... A01N 43/04 |
| WO 97/32990 | 9/1997 | WIPO | ............................ C12N 15/86 |

OTHER PUBLICATIONS

Whalen, G. F. et al. "The Fate of Intravenously Administered bFGF and the Effect of Heparin," (1989) *Growth Factors*, vol. 1, pp. 157–164.

Cuevas, P. et al. "Single Topical Application of Human Recombinant Basic Fibroblast Growth Factor (rbFGF) Promotes Neovascularization in Rat Cerebral Cortex," (1993) *Surg Neurol*, vol. 39, pp. 380–384.

Edelman, E. R. et al. "Perivascular and Intravenous Administration of Basic Fibroblast Growth Factor: Vascular and Solid Organ Deposition," (1993) *Proc Natl Acad Sci USA*, vol. 90, pp. 1513–1517.

Battler, A. et al. "Intracoronary Injection of Basic Fibroblast Growth Factor Enhances Angiogenesis in Infarcted Swine Myocardium," (1993) *JACC*, vol. 22, No. 7, pp. 2001–2006.

Sellke, F. W. et al. "Basic FGF Enhances Endothelium–Dependent Relaxation of the Collateral–Perfused Coronary Microcirculation," (1994) *American Physiological Society*, pp. H1303–H1311.

Riessen, R. et al. "Prospects for Site–Specific Delivery of Pharmacologic and Molecular Therapies," (1994) *JACC*, vol. 23, No. 5, pp. 1234–1244.

Harada, K. et al. "Basic Fibroblast Growth Factor Improves Myocardial Function in Chronically Ischemic Porcine Hearts," (1994) *J Clin Invest*, vol. 94, pp. 623–630.

*Primary Examiner*—John D. Yasko
*Assistant Examiner*—Mannel Mendez
*Attorney, Agent, or Firm*—Townsend and Townsend and Crew LLP

[57] ABSTRACT

Angiogenesis in cardiac and other tissues is promoted by the transmural delivery of angiogenic factors such as VEGF, FGF, EGF, and PDGF, through blood vessels and other body lumens into the surrounding tissue. Usually, the angiogenic factor is delivered using a catheter having infusion parts at its distal end. Optionally, the distal end of the catheter is radially expanded to engage the infusion parts directly against the blood vessel wall.

24 Claims, 5 Drawing Sheets

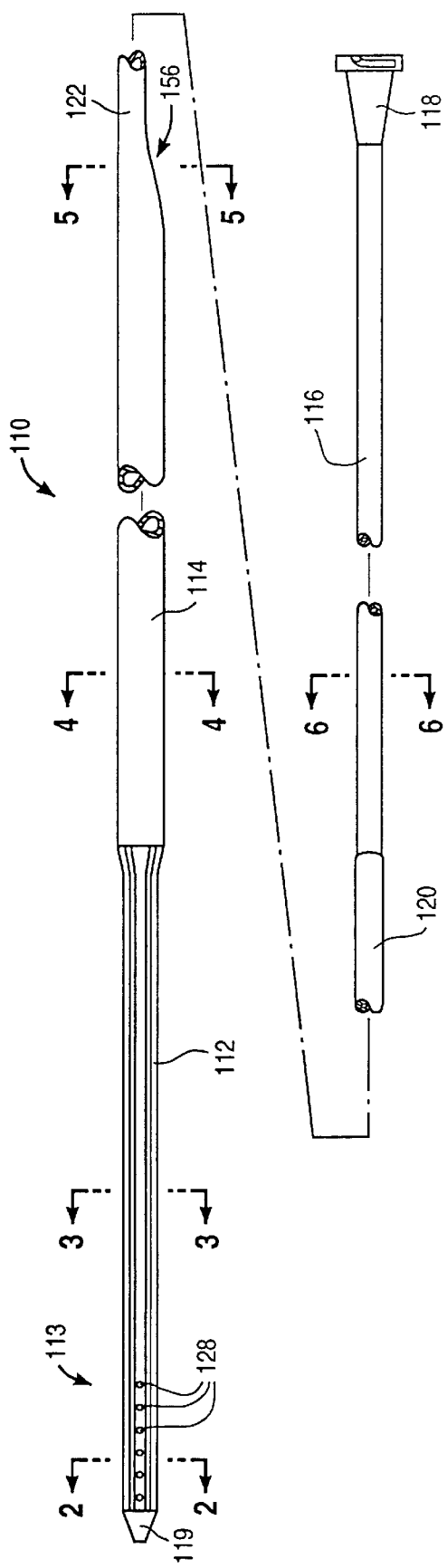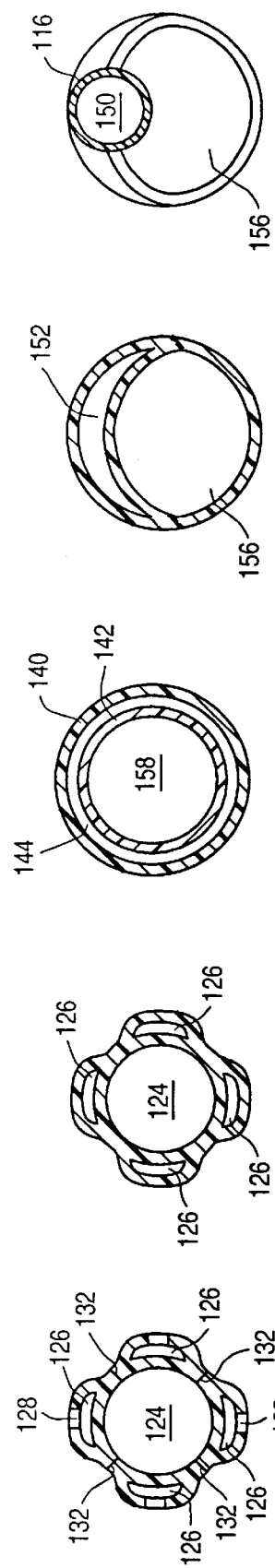
FIG. 1
FIG. 2
FIG. 3
FIG. 4
FIG. 5
FIG. 6

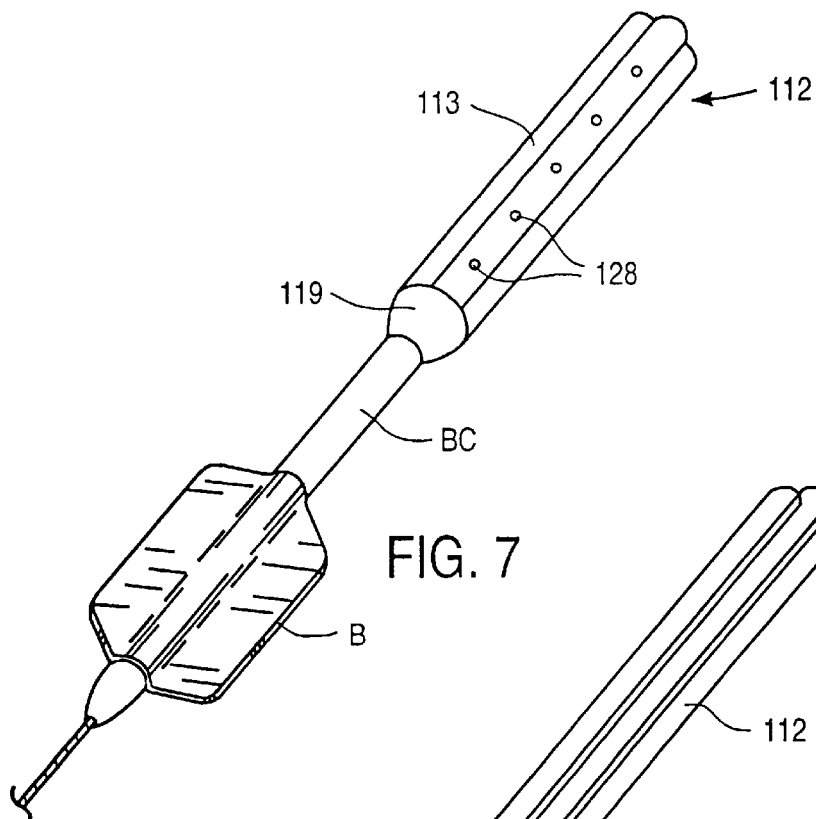
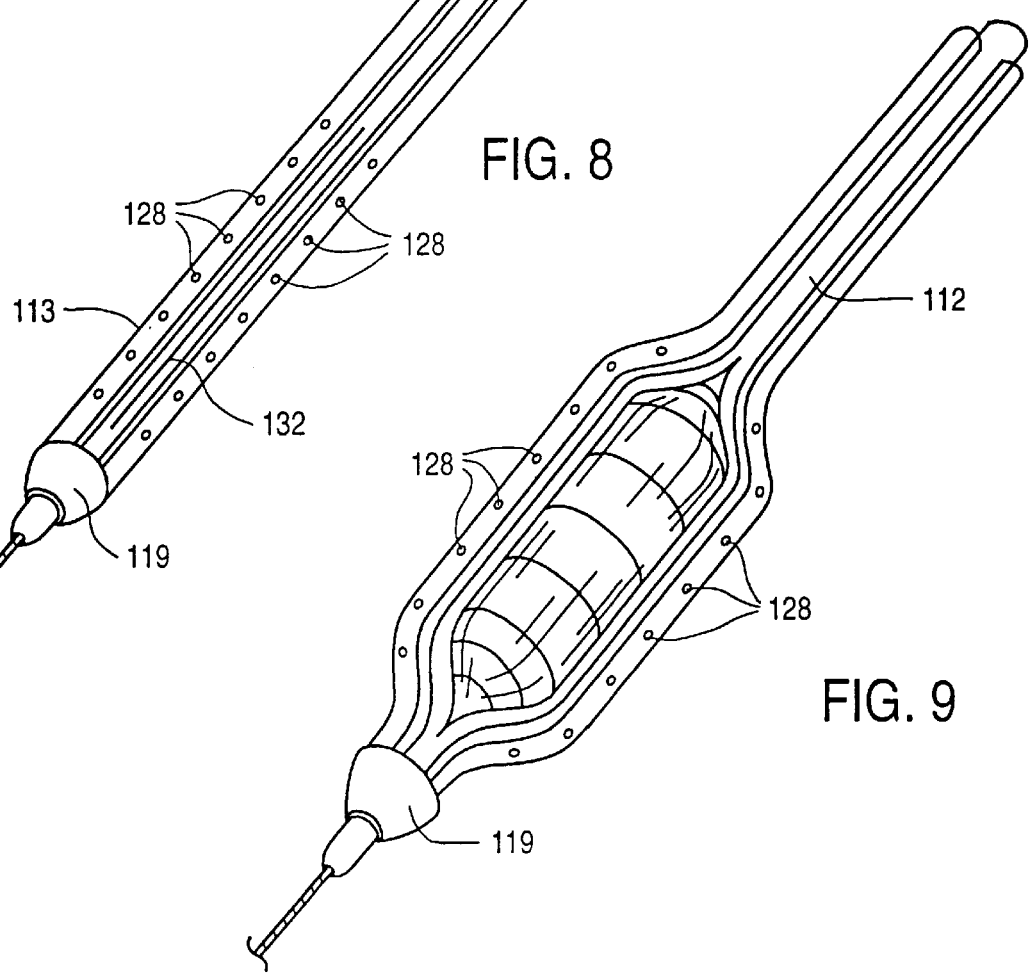

LOCALIZED INTRAVASCULAR DELIVERY OF GROWTH FACTORS FOR PROMOTION OF ANGIOGENESIS

This application claims the benefit of U.S. Provisional Application No. 60/009,086, filed Dec. 22, 1995, the disclosure of which is incorporated by reference.

BACKGROUND OF THE INVENTION

1. Field of the Invention

The present invention relates generally to methods for promoting angiogenesis in tissue surrounding body lumens. More particularly, the present invention relates to methods for promoting angiogenesis in tissue surrounding coronary and peripheral arteries in order to treat ischemia.

Coronary artery disease usually results from the deposition of atheromas in the large and medium-sized arteries supplying the heart. Such blockages of the coronary arteries can in turn cause myocardial ischemia which is a condition characterized by limited and/or irregularly distributed blood flow from the coronary arteries to heart tissue. In severe cases, myocardial ischemia can result in myocardial infarction (heart attack) and sudden cardiac death. Angina pectoris is a chronic condition associated with myocardial ischemia and characterized by chest discomfort as a result of vigorous and in some cases even mild exertion.

Angina pectoris can be treated by the administration of drugs, such as β-adrenergic blocking agents and vasodilators, including nitroglycerin, amyl nitrite, nitrates, and calcium antagonists. While effective for short-term treatment, such drugs are ineffective at treating the arterial blockages responsible for the underlying coronary artery disease. To treat the arterial blockages, various surgical and catheter-based protocols have been developed. The most effective is probably coronary artery bypass surgery, where bypass grafts are surgically implanted around blockages in the coronary arteries. While very effective, coronary artery bypass surgery is highly invasive and results in significant patient morbidity and mortality. Catheter-based interventions, such as balloon angioplasty, laser angioplasty, and atherectomy, are considerably less invasive, but are also less effective, frequently resulting in abrupt closure or restenosis following the intervention.

For these reasons, it would be desirable to provide alternative methods for treating coronary artery disease, where the methods are both effective and minimally invasive. It would be particularly desirable to provide additional catheter-based interventions for treating coronary artery blockages in order to enhance blood perfusion to heart muscle beyond such blockages. More specifically, it would be desirable to provide methods and systems for delivering active agents for promoting angiogenesis to enhance collateral flow to ischemic tissue beds.

2. Description of the Background Art

Periadvential and systemic delivery of bFGF to promote angiogenesis in cardiac tissue are described in Cuevas et al. (1993) Surg. Neurol. 39: 380–384; Selke et al. (1994) Am. J. Physiol. 267: H1303–1311; Harada et al. (1994) J. Clin. Invest. 94: 623–630; Edelman et al. (1993) Proc. Natl. Acad. Sci. USA 90: 1513–1517; and Whalen et al. (1989) Growth Factors 1: 157–164. The effect of direct coronary infusion of bFGF into swine hearts is described in Battler et al. (1993) J. Am. Coll. Cardiol. 22: 2001–2006.

The use of intravascular catheters for delivering particular drugs and classes of drugs is described in U.S. Pat. Nos. 5,180,366; 5,171,217; 5,049,132; and 5,021,044; and PCT Publications WO 93/08866 and WO 92/11895. Riessen et al. (1994) JACC 23: 1234–1244 is a review article discussing the use of catheters and stents for the local delivery of therapeutic agents into the blood vessel wall.

A preferred infusion catheter for delivering an angiogenic factor in accordance with the methods of the present invention is described in copending application Ser. No. 08/473,800, assigned to the assignee of the present invention, filed on Jun. 7, 1995, the full disclosure of which is incorporated herein by reference. This copending application teaches that the catheter may be used for the intravascular delivery of anti-restenotic, anti-proliferative, thrombolytic, fibrinolytic, and other agents useful in connection with angioplasty treatment in a patient's coronary vasculature.

SUMMARY OF THE INVENTION

The present invention provides methods for promoting angiogenesis in tissue surrounding a body lumen, particularly including coronary and other arteries in a region of ischemic tissue. The methods comprise transmurally delivering an angiogenic factor to a target site within the blood vessel. Exemplary angiogenic factors include growth factors, such as fibroblast growth factor (FGF), vascular endothelial growth factor (VEGF), or a combination thereof, and the like. Preferred is the use of VEGF as described in more detail below.

The term "angiogenesis" refers to the growth of blood vessels in tissue in response to stimuli, particularly in response to administration of the angiogenic factor in the manner described below. The present invention will find its greatest use in promoting angiogenesis in ischemic tissues which are deprived of blood perfusion for any reason, such as the result of coronary or peripheral artery disease which deprives the tissue of adequate blood flow.

The term "tissue" refers to any tissue in which angiogenesis may be desired. Tissues to be treated by the present invention will typically be adjacent to blood vessels, more typically being adjacent to coronary and peripheral arteries, where the angiogenic factor is delivered transmurally within the adjacent blood vessel to promote angiogenesis from the delivery site within the blood vessel into the surrounding tissue. The target tissue will usually be ischemic, i.e., deprived of blood flow, but the present invention might also find use with promoting angiogenesis in non-ischemic tissues.

The phrase "body lumen" will generally refer to blood vessels, including portions of the arterial vasculature and venous vasculature. The method of the present invention will find its greatest use in treating ischemic cardiac tissues associated with coronary artery disease.

The phrase "transmural delivery" is defined as localized delivery of the angiogenic factor into the blood vessel or other body lumen wall, including the neointimal, intimal, medial, adventitial and perivascular spaces, adjacent to the target site. Such transmural delivery will typically be effected using an intravascular infusion catheter, as described in detail below, but could also be achieved by the implantation of vascular implants capable of releasing the angiogenic factor over time.

The phrase "angiogenic factor" is defined to include natural and recombinant forms of a variety of peptides, e.g. growth factors and related molecules which are able to promote endothelial and smooth muscle cell proliferation leading to the formation of new blood vessels (angiogenesis) when administered transmurally into blood vessels adjacent to tissue. Exemplary growth factors include fibroblast growth factor (FGF), particularly including basic FGF (bFGF), vascular endothelial growth factor (VEGF), and the like.

Particularly preferred is the delivery of VEGF as described in more detail below.

In a first particular aspect of the present invention, a method for promoting angiogenesis in tissue surrounding a blood vessel comprises advancing a distal end of a catheter to a target site within the blood vessel. An amount of an angiogenic factor sufficient to promote angiogenesis in tissue surrounding the target site is then delivered through the distal end of the catheter. Usually, the catheter is introduced percutaneously to the patient's vasculature and advanced transluminally to the target site.

The angiogenic factor is then delivered from a proximal end of the catheter, through a lumen in the catheter body, and to the distal end from where it is released into the blood vessel wall. The angiogenic factor will penetrate the vascular wall into the perivascular space surrounding the blood vessel, thus providing the desired angiogenesis. Optionally, the distal end of the catheter may be expanded to engage infusion ports therein against the blood vessel wall to enhance transmural penetration. Further optional, needles or other penetrating elements may be provided on the catheter to enhance infusion of the angiogenic factor into and through the vessel wall.

In a second particular aspect of the present invention, a method for promoting angiogenesis in tissue surrounding a stenotic region in a coronary artery comprises transluminally advancing a distal end of an infusion catheter to the stenotic region in the artery. A distal end of the infusion catheter is expanded to engage infusion ports therein against the luminal wall of the artery, preferably by positioning a balloon within the distal end of the infusion catheter and inflating the balloon to a predetermined inflation pressure. An amount of an angiogenic factor sufficient to promote angiogenesis in tissue surrounding the target site is then delivered through the infusion ports, usually at a predetermined infusion pressure which is independent of the balloon inflation pressure.

The angiogenic factor may be delivered to the target site in the blood vessel or other body lumen as a bolus, but will more usually be delivered in a continuous or discontinuous stream over an extended time period. The total amount of the angiogenic factor delivered to the target site is typically in the range from 0.1 µg/kg to 100 mg/kg, more typically from 1 µg/kg to 10 mg/kg (body weight). When delivered continuously, the time period of delivery will usually be in the range from 1 second to 24 hours, more usually being from 2 seconds to 30 minutes, even more preferably from 5 seconds to 5 minutes although delivery times more than three minutes may require a delivery system that provides for blood perfusion to the distal vasculature. The time of delivery can be extended to days or weeks, or longer, when controlled release implanted devices, such as stents, endoluminal paving delivery, sustained release polymers, timed release particles, or the like are employed.

BRIEF DESCRIPTION OF THE DRAWINGS

FIG. 1 is a side view of a sleeve catheter incorporating drug delivery lumens useful in performing the methods of the present invention.

FIGS. 2–6 are cross-sectional views taken along lines 2–6 in FIG. 1, respectively.

FIGS. 7–9 illustrate the use of a balloon catheter to expand the distal end of the catheter of FIGS. 1–6.

DESCRIPTION OF THE SPECIFIC EMBODIMENTS

Figure 10B:
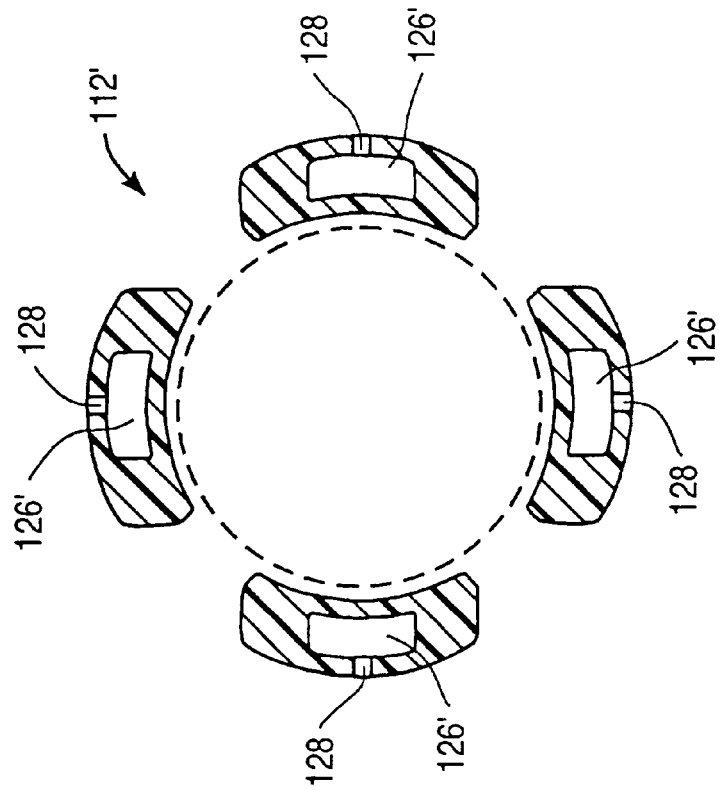
FIGS. 10A and 10B are cross-sectional views of the distal region of the catheter of FIG. 1 shown in its non-expanded (FIG. 10A) and expanded (FIG. 10B) configurations.

The methods of the present invention rely on the transmural delivery of an angiogenic factor to a target location within a blood vessel or other body lumen to promote angiogenesis in tissue surrounding the body lumen. The methods of the present invention are particularly useful for treating ischemic tissue surrounding blood vessels, and more particularly useful for treating ischemic cardiac tissues surrounding occluded, partially occluded, and other coronary arteries.

The methods of the present invention will usually be employed as a primary treatment modality, i.e., without employing other drug, surgical, and/or catheter-based interventional therapies. The methods of the present invention, however, could be employed in combination with other treatment modalities. For example, delivery of angiogenic factors according to the methods of the present invention could be performed after balloon angioplasty to enhance blood perfusion into ischemic tissue surrounding the treated stenotic region. Delivery of angiogenic factors could also be combined with delivery of other therapeutic agents intended for treating coronary artery disease, such as anti-thrombotic and fibrinolytic agents.

Angiogenic factors suitable for use in the present invention include a variety of known growth factors, such as fibroblast growth factors (FGF's), particularly including basic FGF (bFGF) and acidic FGF (aFGF); epidermal growth factor (EGF); platelet-derived growth factor (PDGF); vascular endothelial growth factor (VEGF); and the like. The phrases "FGF polypeptide," "VEGF polypeptide," "EGF polypeptide," and "PDGF polypeptide" are defined to include natural and recombinant forms of the full length proteins as well as fragments, analogs, mimetics, and other related molecules having similar or identical angiogenic activity when administered transmurally as described herein.

Transmural deliver of angiogenic factors according to the methods of the present invention, may be accomplished using any of a variety of known intravascular drug delivery systems. Most commonly, the angiogenic factors will be delivered using intravascular catheter delivery systems as described in greater detail below. In some cases, however, it may be advantageous to employ implanted devices, such as implanted stents capable of delivering angiogenic factors for prolonged periods of time. See, for example, U.S. Pat. No. 5,342,348 and EP 604 022, which describe stent apparatus capable of releasing a variety of drugs over time. Such stent apparatus would be suitable for transmural delivery of angiogenic factors according to the method of the present invention.

A variety of catheter systems useful for the direct transmural infusion of angiogenic factors into the blood vessel wall are also well-described in the patent literature. Most commonly, balloon catheters having expandable distal ends capable of engaging the inner wall of a blood vessel and infusing an angiogenic factor directly therein are well-described in the patent literature. See, for example, U.S. Pat. Nos. 5,318,531; 5,304,121; 5,295,962; 5,286,254; 5,254,089; 5,213,576; 5,197,946; 5,087,244; 5,049,132; 5,021,044; 4,994,033; and 4,824,436. Catheters having spaced-apart or helical balloons for expansion within the lumen of a blood vessel and delivery of a therapeutic agent to the resulting isolated treatment site are described in U.S. Pat. Nos. 5,279,546; 5,226,888; 5,181,911; 4,824,436; and 4,636,195. A particular drug delivery catheter is commercially available under the trade name Dispatch™ from SciMed Life Systems, Inc., Maple Grove, Minn. Non-balloon drug deliver catheters are described in U.S. Pat. Nos. 5,180,366; 5,112,305; and 5,021,044; and PCT Publication WO 92/11890. Ultrasonically assisted drug delivery catheters (phonophoresis devices) are described in U.S. Pat. Nos. 5,362,309; 5,318,014; and 5,315,998. Other iontophoresis and phonophoresis drug delivery catheters are described in U.S. Pat. Nos. 5,304,120; 5,282,785; and 5,267,985. Finally, sleeve catheters having drug delivery lumens intended for use in combination with conventional angioplasty balloon catheters are described in U.S. Pat. Nos. 5,364,356 and 5,336,178.

Any of the catheters described in the above-listed patents may be employed for delivering angiogenic factors according to the method of the present invention. Full disclosures of each of these patent references are hereby incorporated herein by reference.

It would also be possible to deliver angiogenic factors by applying a thin layer of a hydrogel, glycosaminoglycans, or other polymeric carrier matrix to the endoluminal wall at the target location. Usually, the polymeric carrier will be biodegradable or bioeluting and serve as a temporary wall support while the angiogenic factors are released over time. Such endoluminal paving systems are described in, for example, U.S. Pat. No. 5,328,471 and Slepian (1994) Card. Clin. 12: 715–737.

The angiogenic factors used in the methods of the present invention will be incorporated into conventional pharmaceutical compositions for transmural delivery. In the case of continuous catheter delivery, the angiogenic factors will be incorporated into an acceptable fluid carrier, e.g., being formulated with sterile water, isotonic saline, glucose solution, or the like. The formulations may contain pharmaceutically acceptable auxiliary substances as are generally used in pharmaceutical preparations, including buffering agents, tonicity adjusting agents, such as sodium acetate, sodium lactate, sodium chloride, potassium chloride, and calcium chloride, and the like. The concentration of the angiogenic factors in the liquid formulation may vary widely, from 0.001% to 20%, typically being from 0.01% to 1% by weight. General methods for preparing such pharmaceutical formulations are described in *Remington's Pharmaceutical Sciences*, Mack Publishing Co., Philadelphia, Pa., 1985.

The pharmaceutical compositions will be delivered for a time sufficient to achieve the desired physiological effect, i.e., the promotion of blood vessel growth in tissue surrounding the target site in the blood vessel. Generally, the total amount of the angiogenic factor delivered based on patient body weight will be from 0.1 μg/kg to 100 mg/kg, usually from 1 μg/kg to 10 mg/kg. These amounts can be delivered as a bolus, i.e., in a single amount released over a very short time period, typically on the order of seconds, but will more usually be delivered as a continuous stream (or discontinuous stream, e.g., a series of short pulses) of a fluid pharmaceutical formulation over time. The total amount of time will, of course, depend on the delivery rate and drug concentration in the fluid being delivered, typically being from 1 second to 24 hours, more usually from 2 seconds to 30 minutes and even more usually from 5 seconds to 5 minutes.

The pharmaceutical formulations delivered according to the methods of the present invention may include other active agents in addition to the angiogenic factor(s). In particular, the formulations may include anti-coagulants and anti-thrombotic agents, such as heparin, low molecular weight heparin, and the like.

Referring now to FIGS. 1–6, a particular drug delivery catheter in the form of a sleeve infusion catheter 110 useful for delivering angiogenic factors according to the methods of the present invention will be described. Such infusion catheters are described in greater detail in copending application Ser. No. 08/473,800, filed on Jun. 7, 1995, assigned to the assignee of the present application, the full disclosure of which has previously been incorporated herein by reference.

The infusion sleeve catheter 110 comprises a radially expansible infusion sleeve 112, a radially expansible portion 113 within the sleeve 112, a manifold section 114, and a shaft 116. A hub 118 is attached to the proximal end of the shaft 116 and may be connected to a source of infusion fluid, such as a syringe, pump, or the like. An atraumatic tip 119 is secured to the distal end of the sleeve 112. Distal end 120 of the shaft is secured within a proximal tubular extension 122 of the manifold structure 114. As illustrated in FIGS. 1–6, the shaft 116 is a metal hypo tube having a circular cross-sectional area. The length of the shaft will depend on the length of the other portions of the catheter 110, with the overall length of the catheter typically being about 90 to 150 cm for coronary applications introduced through the femoral artery, as described in more detail below.

The radially expansible infusion sleeve 112 comprises a central receptacle 114 (FIGS. 2 and 3) and four infusion lumens 126. Infusion ports 128 are formed over the distal-most 2.5 to 10 cm of the expansible portion 113 of the sleeve 112. Usually, the expansible portion 113 of the sleeve is axially split along lines 132 (FIG. 2) to permit radial expansion, as illustrated in FIG. 9 described below. The distal ends of the lumens 126 will be sealed, typically by the tip 119. Other structures for providing radial expansibility are described above.

The manifold structure 114 comprises an outer sheath or tube 140 coaxially received over an inner tube 142. Annular lumen 144 directs infusate into the infusion lumens 126. The annular lumen 144 is connected to lumen 150 and shaft 116 (FIG. 6) by a crescent-shaped transition lumen region 152 (FIG. 5) which is formed near the balloon catheter entry port 156. The balloon entry port 156 opens into a catheter lumen 158, which in turn leads into the balloon receptacle 124, typically having a cross-sectional area in the range from 0.5 mm$^2$ to 2 mm$^2$, typically about 1.25 mm$^2$.

Referring now to FIGS. 7–9, a balloon catheter BC having an inflatable balloon B may be introduced through entry port 156 so that the balloon B extends outward through the distal tip of the sleeve 112. The balloon may then be inflated and deflated while the infusion sleeve 112 remains retracted. After the balloon B is deflated, the sleeve 112 may be advanced distally over the balloon, as illustrated in FIG. 8. By then inflating the balloon, the expansible portion 113 of the sleeve 112 will be expanded, as illustrated in FIG. 9.

Figure 10A:
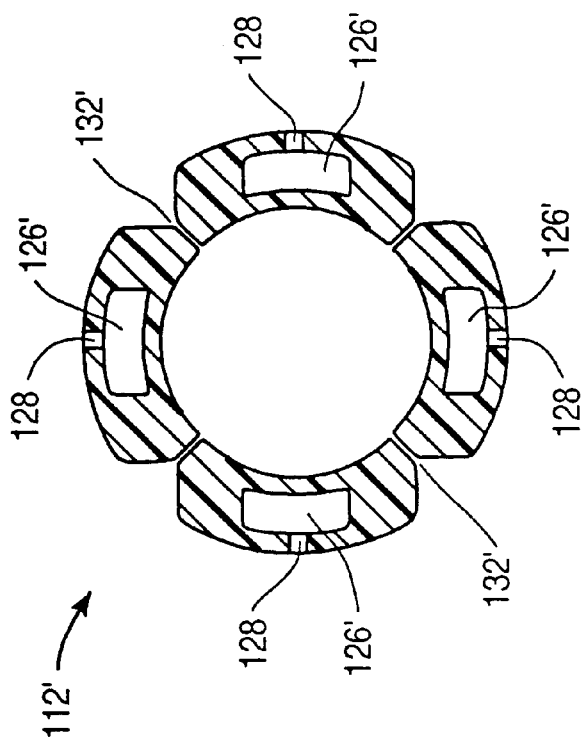

The infusion sleeve 112 may have an alternative cross-section, as illustrated in FIGS. 10A and 10B. The sleeve 112' may be formed with lumens 126' formed within the wall of the catheter, rather than on the outer surface of the catheter as illustrated in FIGS. 1–9. The wall thickness in these constructions will typically be slightly greater, usually being in the range from 0.2 mm to 0.4 mm. The wall will be axially split along lines 132' in order to allow expansion, as shown in FIG. 10B.

Figure 11:
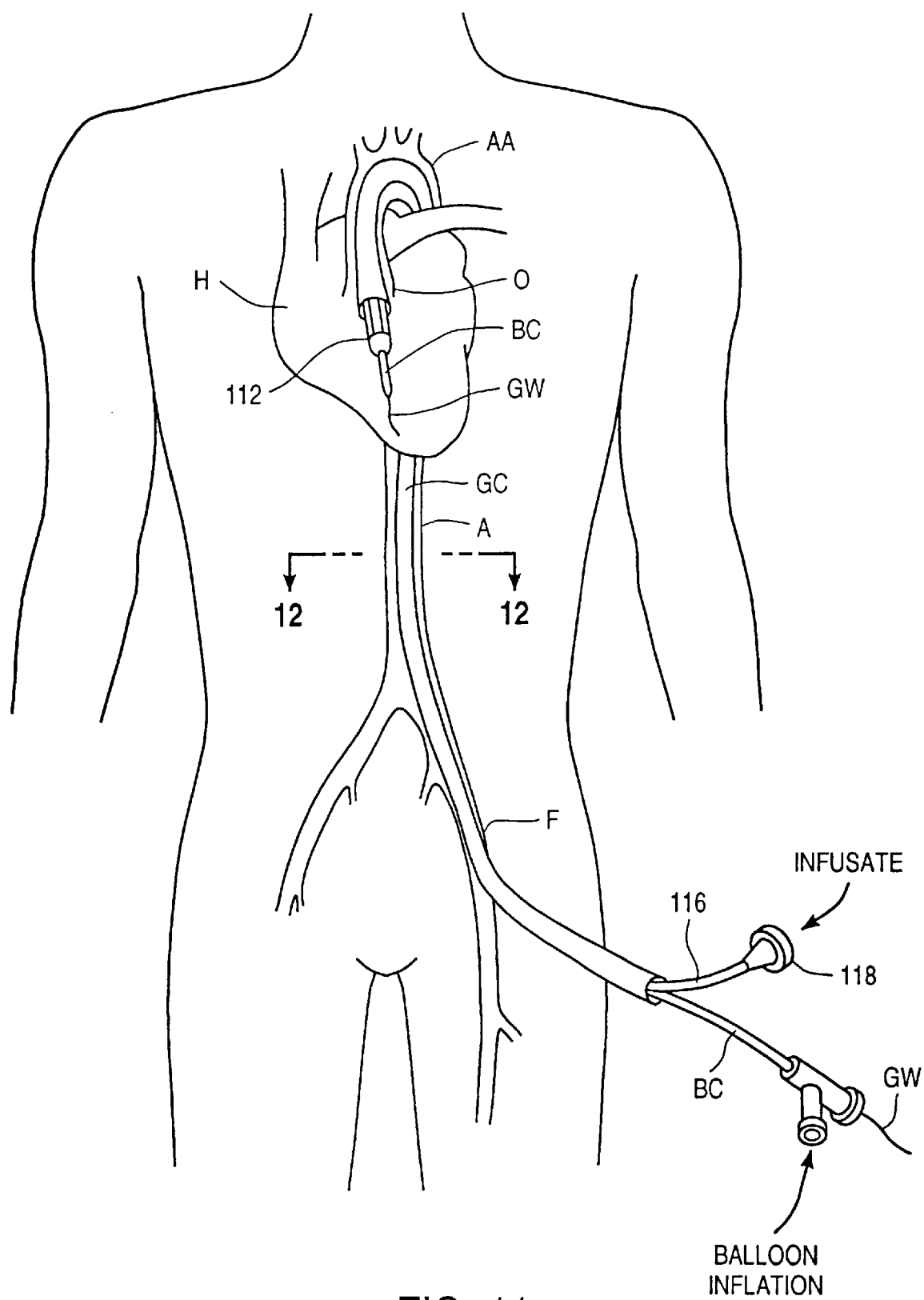
FIG. 11 illustrates the use of the catheter of FIG. 1 to deliver an angiogenic factor to a coronary artery in combination with an angioplasty balloon catheter in accordance with the method of the present invention.
Figure 12:
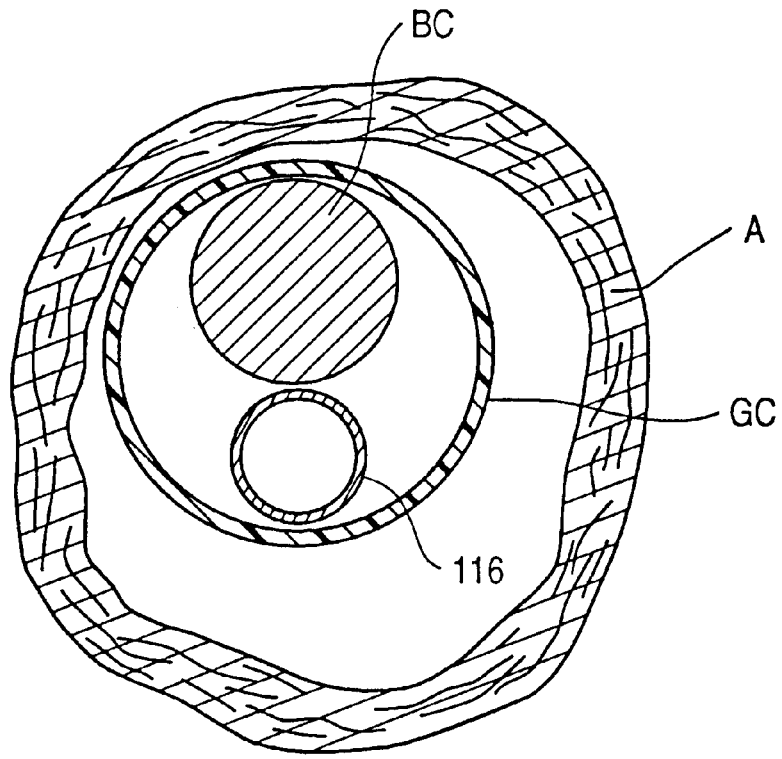
FIG. 12 is a cross-sectional view taken along line 12—12 of FIG. 11.
Figure 13:
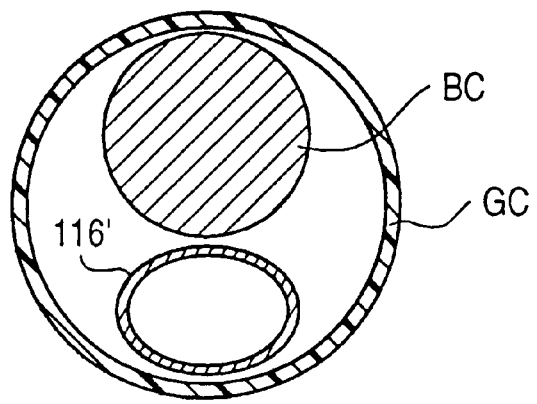
FIG. 13 is an alternative cross-sectional view similar to FIG. 12.

Infusion catheter 110 may be introduced through conventional guiding catheter GC to position the infusion sleeve 12 within a coronary artery in the patient's heart H, as illustrated in FIG. 11. Guiding catheter GC may be any conventional guiding catheter intended for insertion into the femoral artery F, then via the patient's aorta A around the aortic arch AA, to one coronary ostia O. Such guiding catheters are commercially available through a number of suppliers, including Medtronic, Minneapolis, Minn., available under the tradename Sherpa™. Specific guiding catheters are available for introducing catheters to either the left main or the right coronary arteries. Such guiding catheters are manufactured in different sizes, typically from 7F to 10F when used for coronary interventional procedures.

According to the method of the present invention, the balloon catheter BC is introduced through the balloon entry port 156, as described previously in connection with FIGS. 7–9. The atraumatic tip 119 of the infusion sleeve 112 will be positioned proximally of the balloon, typically by a distance in the range from 25 cm to 35 cm. The combination of the balloon catheter BC, and infusion catheter 110 will be introduced through the guiding catheter GC over a conventional guidewire GW until the balloon is positioned within the target site within the coronary artery. Preferably, the infusion sleeve 112 will remain positioned entirely within the guiding catheter GC while the balloon B of the balloon catheter BC is initially located at the target site. The balloon may then be expanded to treat other regions within the coronary vasculature in a conventional manner. After the angioplasty treatment is completed, the infusion sleeve 112 will be advanced distally over the balloon catheter BC until the radially expansible portion is properly positioned over the balloon. Such positioning can be confirmed by proper alignments of radiopaque markers on the infusion sleeve 112 (not shown) with markers on the balloon catheter, typically within the balloon itself. After the infusion sleeve is properly positioned, the balloon B on the balloon catheter BC will be inflated to engage the infusion ports 128 against the inner wall of coronary artery.

The angiogenic factor is then delivered through the hub 118 for desired treatment. Typically, the angiogenic factor will be delivered at a flow rate from 10 ml/min to 40 ml/min, preferably from 20 ml/min to 30 ml/min. Infusion proximal pressures will typically be in the range of 30 psi to 150 psi, preferably from 70 psi to 110 psi. Balloon inflation pressures during infusion will typically be in the range from 0.5 atm to 6 atm, preferably from 1 atm to 2 atm. Specific treatment pressures, times, and other conditions will depend on the nature of the infusate and condition being treated. Typically, treatment periods will not exceed 5 mins., usually not exceed 3 mins. in order not to occlude the blood vessel for a longer time than is tolerable to the patient. Treatment protocols can be extended, however, by repetitively administering the infusate, i.e., deflating the balloon to reestablish coronary perfusion and then re-inflating the balloon and delivering infusate after a time sufficient to perfuse the distal coronary tissue. Such delivery steps can be repeated two, three, or more times as necessary to achieve a desired effect.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for promoting angiogenesis in tissue surrounding a body lumen, said method comprising transmurally delivering an angiogenic factor at a target site within the body lumen.

2. A method as in claim 1, wherein the angiogenic factor is selected from the group consisting of a VEGF polypeptide, an FGF polypeptide, an EGF polypeptide, and a PDGF polypeptide.

3. A method as in claim 1, wherein the angiogenic factor is delivered in an amount in the range from 0.1 $\mu$g to 100 mg per kilogram of body weight.

4. A method as in claim 1, wherein the angiogenic factor is delivered over a time period in the range from 1 second to 24 hours.

5. A method for promoting angiogenesis in tissue surrounding a blood vessel, said method comprising:

advancing a distal end of a catheter to a target site within the blood vessel; and delivering through the distal end of the catheter and transmurally through the blood vessel wall an amount of an angiogenic factor sufficient to promote angiogenesis in tissue surrounding the target site.

6. A method as in claim 5, wherein the angiogenic factor is selected from the group consisting of a VEGF polypeptide, an FGF polypeptide, an EGF polypeptide, and a PDGF polypeptide.

7. A method as in claim 5, wherein the angiogenic factor is delivered in an amount in the range from b 0.1$\mu$g to 100 mg per kilogram of body weight.

8. A method as in claim 5, wherein the angiogenic factor is delivered over a time period in the range from 1 second to 24 hours.

9. A method as in claim 5, wherein the distal end of the catheter is introduced percutaneously to a patient's vasculature and advanced transluminally to the target site.

10. A method as in claim 9, wherein the angiogenic factor is delivered from the proximal end of the catheter, through a lumen in the catheter, to the distal end.

11. A method as in claim 5, further comprising expanding the distal end of the catheter to engage a plurality of infusion ports against the blood vessel wall wherein the angiogenic factor is delivered through said infusion port.

12. A method as in claim 11, wherein the expanding step comprises:

positioning a balloon within the distal end of the catheter; and inflating the balloon to a predetermined inflation pressure.

13. A method as in claim 12, wherein the delivering step comprises supplying fluid containing the angiogenic factor to the ports at a predetermined infusion pressure, wherein the infusion pressure is independent of the inflation pressure.

14. A method as in claim 11, wherein the expanding step comprises inflating the distal end of the catheter having the infusion ports with a fluid carrying the angiogenic factor so that said fluid is released through the infusion ports.

15. A method for promoting angiogenesis in tissue surrounding a stenotic region in a coronary artery, said method comprising:

advancing transluminally a distal end of an infusion catheter to the stenotic region in the artery;

radially expanding an array of infusion ports on the distal end of the infusion catheter to engage said ports against the luminal wall of the blood vessel; and delivering through the infusion ports into the blood vessel wall an amount of an angiogenic factor sufficient to promote angiogenesis in tissue surrounding the target site.

16. A method as in claim 15, wherein the angiogenic factor is selected from the group consisting of a VEGF polypeptide, an FGF polypeptide, an EGF polypeptide, and a PDGF polypeptide.

17. A method as in claim 15, wherein the angiogenic factor is delivered in an amount in the range from 0.1 µg to 100 mg per kilogram of body weight.

18. A method as in claim 15, wherein the angiogenic factor is delivered over a time period in the range from 1 second to 24 hours.

19. A method as in claim 15, wherein the distal end of the catheter is introduced percutaneously to a patient's vasculature prior to transluminal advancement to the target site.

20. A method as in claim 19, wherein the angiogenic factor is delivered from the proximal end of the catheter, through a lumen in the catheter, to the distal end.

21. A method as in claim 15, further comprising expanding the distal end of the catheter to engage a plurality of infusion ports against the blood vessel wall, wherein the angiogenic factor is delivered through said infusion port.

22. A method as in claim 15, wherein the radially expanding step comprises:

positioning a balloon within the distal end of the infusion catheter, and inflating the balloon to a predetermined inflation pressure.

23. A method as in claim 22, wherein the delivering step comprises supplying fluid containing the angiogenic factor to the infusion ports at a predetermined infusion pressure, wherein the infusion pressure is independent of the inflation pressure.

24. A method as in claim 15, wherein the radially expanding step comprises inflating the distal end of the infusion catheter having the infusion ports with a fluid carrying the angiogenic factor so that said fluid is released through the infusion ports.

* * * * *